(12) United States Patent
Cheng et al.

(10) Patent No.: US 9,993,155 B2
(45) Date of Patent: Jun. 12, 2018

(54) LENS MODULE AND EYE FUNDUS CAMERA USING THE SAME

(71) Applicant: Medimaging Integrated Solution, Inc., Hsinchu (TW)

(72) Inventors: Chu-Ming Cheng, Hsinchu (TW); Long-Sheng Liao, Hsinchu (TW)

(73) Assignee: MEDIMAGING INTEGRATED SOLUTION, INC., Hsinchu (TW)

( * ) Notice: Subject to any disclaimer, the term of this patent is extended or adjusted under 35 U.S.C. 154(b) by 0 days. days.

(21) Appl. No.: 14/149,206

(22) Filed: Jan. 7, 2014

(65) Prior Publication Data

US 2014/0198299 A1 Jul. 17, 2014

(30) Foreign Application Priority Data

Jan. 11, 2013 (TW) .............................. 102101066 A

(51) Int. Cl.
| | |
|---|---|
| *G02B 9/14* | (2006.01) |
| *A61B 3/12* | (2006.01) |
| *A61B 3/00* | (2006.01) |
| *A61B 3/14* | (2006.01) |
| *G02B 9/12* | (2006.01) |

(52) U.S. Cl.
CPC ............. *A61B 3/12* (2013.01); *A61B 3/0091* (2013.01); *A61B 3/14* (2013.01); *G02B 9/12* (2013.01); *G02B 9/14* (2013.01); *A61B 3/1208* (2013.01)

(58) Field of Classification Search
CPC .... G02B 9/14; G02B 9/12; A61B 3/14; A61B 3/10; A61B 3/107

USPC .................. 351/207, 221; 359/785
See application file for complete search history.

(56) References Cited

U.S. PATENT DOCUMENTS

| | | | | |
|---|---|---|---|---|
| 4,132,466 A | * | 1/1979 | Matsumura ............ | A61B 3/156 351/207 |
| 4,439,024 A | * | 3/1984 | Ito ............................ | A61B 3/14 351/207 |
| 4,483,597 A | * | 11/1984 | Mihara ................... | G02B 13/02 359/745 |
| 4,502,766 A | * | 3/1985 | Ito ............................ | A61B 3/14 351/206 |
| 5,455,644 A | * | 10/1995 | Yazawa .................. | A61B 3/145 351/206 |
| 7,048,379 B2 | * | 5/2006 | Miller ..................... | A61B 3/156 351/205 |

(Continued)

*Primary Examiner* — Zachary Wilkes
(74) *Attorney, Agent, or Firm* — Muncy, Geissler, Olds & Lowe, P.C.

(57) ABSTRACT

A lens module comprises a first lens group, a second lens group and a third lens group, which are arranged from an eye fundus side to an image side in sequence. The first lens group has a positive effective focal length (EFL) and includes a first lens having two convex surfaces respectively facing the eye fundus side and the image side. The second lens group has a positive or negative EFL and includes a plurality of second lenses, wherein the second lens closest to the eye fundus side has a concave surface facing the eye fundus side. The third lens group has a positive EFL and includes a plurality of third lenses, wherein at least one third lens is a cemented lens. The abovementioned lens module decreases the volume of a lens module and reduces the ghosting effect. An eye fundus camera using the abovementioned lens module is also disclosed.

12 Claims, 5 Drawing Sheets

(56) References Cited

U.S. PATENT DOCUMENTS

| | | | |
|---|---|---|---|
| 7,174,094 B2* | 2/2007 | Steinkamp | A61B 3/14 351/221 |
| 2012/0092619 A1* | 4/2012 | Rowe | A61B 3/0016 351/221 |

* cited by examiner

LENS MODULE AND EYE FUNDUS CAMERA USING THE SAME

BACKGROUND OF THE INVENTION

1. Field of the Invention

The present invention relates to a lens module and an eye fundus camera, particularly to a compact handheld lens module and an eye fundus camera using the same.

2. Description of the Prior Art

In an eye fundus observation device, light is guided to the eye fundus of a testee, and then the eye fundus is imaged on the eye of the tester or a photosensor of a camera (such as a film or an image sensor of the camera). The conventional eye fundus observation devices include the direct ophthalmoscope, the indirect ophthalmoscope and the eye fundus camera. Different from the direct ophthalmoscope, the indirect ophthalmoscope forms an intermediary image of the eye fundus in advance and then projects the intermediary image onto the eye of the tester or the photosensor of a camera. The eye fundus camera captures and records the images of the eye fundus of a testee, and the image records are convenient to store and transfer.

The conventional eye fundus observation deices respectively have their disadvantages. For example, the direct ophthalmoscope has an observation angle of merely about 5 degrees and thus can only observe the optic disc or the fovea centralis. Besides, the user of the direct ophthalmoscope must be very close to the testee. The indirect ophthalmoscope has a wider observation field and can also observe the ocular capillaries in addition to the optic disc and the fovea centralis. However, the user of the indirect ophthalmoscope still has to approach the testee very closely. Further, neither the direct ophthalmoscope nor the indirect ophthalmoscope can record the image of the eye fundus of the testee. The eye fundus camera has a wider observation field and a capability of observing and recording the eye fundus of the testee and exempts the tester from closely approaching the testee. However, the eye fundus camera is bulky, hard to carry about and unlikely to apply to some special testees, such as infants, bedridden patients or handicapped patients. Neither the current handheld ophthalmoscope nor the current handheld eye fundus camera provides a precision light beam to guide the testee to accurately adjust the angle of his eyeball for shooting different regions of the eye fundus. Although the desktop eye fundus camera provides a precision light beam, it occupies considerable space.

Accordingly, the manufacturers are eager to develop an eye fundus observation device not only having the above-mentioned advantages but also having reduced volume.

SUMMARY OF THE INVENTION

The present invention is directed to a lens module and an eye fundus camera, wherein the illumination system and the imaging system share a common set of lens groups for reducing volume, and wherein the set of shared lens groups has biconvex surfaces for decreasing the incidence to the imaging system of the light reflected by the shared lens groups and reducing the ghosting effect.

In one embodiment, the proposed lens module is used to converge an image light beam reflected from the eye fundus and comprises a first lens group, a second lens group and a third lens group, which are arranged from the object side to the image side in sequence, and a first light emitting element. The first lens group has a positive effective focal length and is a single whole lens having two convex surfaces respectively facing the object side and the image side. The second lens group has a negative effective focal length and includes a plurality of second lenses, wherein a lens of the second lenses closest to the object side has a concave surface facing the object side. The third lens group has a positive effective focal length and includes a plurality of third lenses, wherein at least one third lens is a cemented lens. The first light emitting element is arranged in the image side of the first lens group and at a single position separated from a surface of the first lens, which faces the image side, by a distance of 40-100 mm, and deviated from an optical axis of the lens module, and which is used to generate an illumination light beam and directly irradiate the first lens group to define an illumination range on said first lens group, wherein the illumination light beam is converged solely by the first lens group to a cornea on the object side and said illumination range contains a central area of said first lens group.

In one embodiment, the proposed eye fundus camera comprises an image sensing module and a lens module. The image sensing module senses light and forms an image. The lens module converges an image light beam, which is reflected from the eye fundus, to the image sensing module. The lens module comprises a first lens group, a second lens group and a third lens group, which are arranged from the object side to the image side in sequence, and a first light emitting element. The first lens group has a positive effective focal length and is a single whole lens having two convex surfaces respectively facing the object side and the image side. The second lens group has a negative effective focal length and includes a plurality of second lenses, wherein a lens of the second lenses closest to the object side has a concave surface facing the object side. The third lens group has a positive effective focal length and includes a plurality of third lenses, wherein at least one third lens is a cemented lens. The first light emitting element is arranged in the image side of the first lens group and at a single position separated from a surface of the first lens, which faces the image side, by a distance of 40-100 mm, and deviated from an optical axis of the lens module, and which is used to generate an illumination light beam and directly irradiate the first lens group to define an illumination range on said first lens group, wherein the illumination light beam is converged solely by the first lens group to a cornea on the object side and said illumination range contains a central area of said first lens group.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENT

The detailed explanation of the present invention is described as follows. The described preferred embodiments are presented for purposes of illustrations and description, and they are not intended to limit the scope of the present invention.

Figure 1:
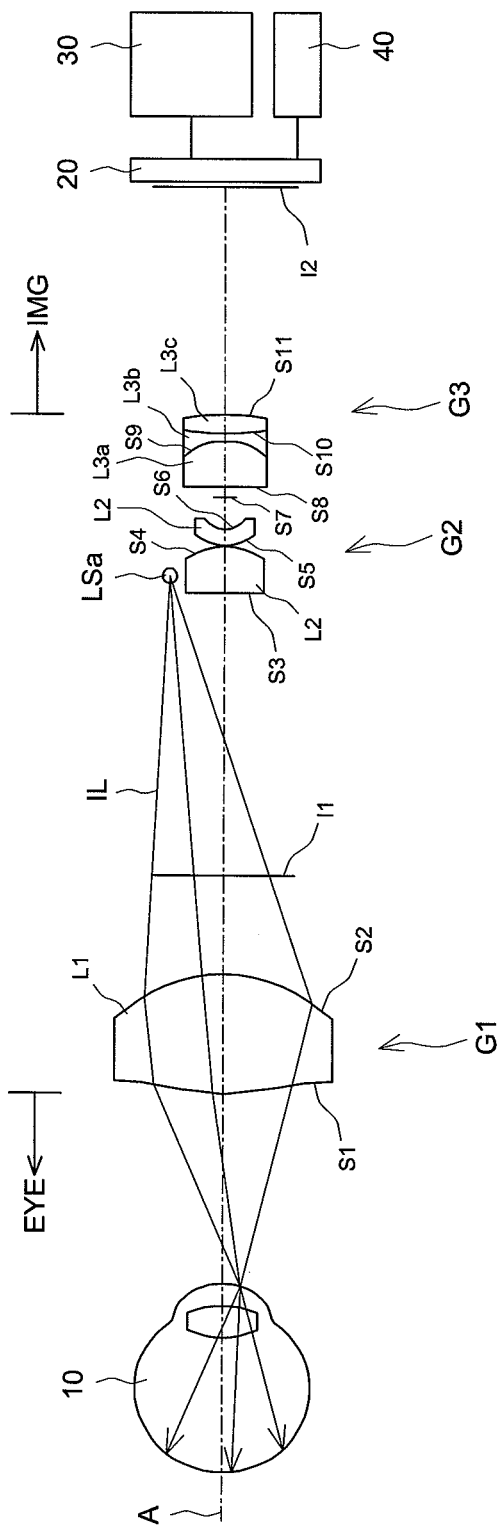
FIG. 1 schematically shows a lens module and an eye fundus camera according to a first embodiment of the present invention.

Refer to FIG. 1. In one embodiment, the lens module of the present invention is used to converge an image light beam reflected from the fundus of an eyeball 10 of a testee to form an image I2. The lens module of the present invention comprises a first lens group G1, a second lens group G2 and a third lens group G3, which are arranged from the eye fundus side EYE (i.e. the object side) to the image side IMG in sequence. The first lens group G1 has a positive effective focal length and includes a first lens L1 having two convex surfaces S1 and S2 respectively facing the eye fundus side EYE and the image side IMG. In one embodiment, the first lens group G1 may be a single piece of lens or a group of cemented lenses.

The second lens group G2 has a positive or negative effective focal length and includes a plurality of second lenses L2, wherein the second lens L2 closest to the eye fundus side EYE has a concave surface S3 facing the eye fundus side EYE. The third lens group G3 has a positive effective focal length and includes a plurality of third lenses, wherein at least one third lens is a cemented lens. For example, in the embodiment shown in FIG. 1, the third lens group G3 includes three third lenses L3a, L3b and L3c, and the third lens L3b is a cemented lens.

Refer to FIG. 1 again. In one embodiment, the lens module of the present invention further comprises a first light emitting element LSa arranged in the image side IMG of the first lens group G1 and deviated from an optical axis A of the lens module. As shown in FIG. 1, the first light emitting element LSa generates an illumination light beam IL. The illumination light beam IL is converged by the first lens group G1 to a cornea in the eye fundus side EYE. According to the foregoing structure, the imaging system and the illumination system share the first lens group G1. The image light beam reflected from the eye fundus is converged by the first lens group G1 to form an intermediary image I1; the intermediary image I1 is further processed by the second lens group G2 and the third lens group G3 to form an image I2. The image I2 is directly observed by an observer or sensed by an image sensing module 20.

Preferably, the positions of the first light emitting element LSa and the cornea of the eyeball 10 with respect to the first lens group G1 meet the object-image relationship. In other words, the first light emitting element LSa is arranged in the object side of the first lens group G1, and the illumination light beam IL emitted by the first light emitting element LSa is converged at the cornea of the eyeball 10 (i.e. the image side) and incident to the fundus of the eyeball 10. It should be noted that the image side mentioned herein is not the image side IMG of the lens module but the image side of the illumination system. According to optics design, the first light emitting element LSa is arranged at a position separated from the surface S2 of the first lens L1, which faces said image side, by a distance of 40-100 mm. According to the foregoing structure, the first light emitting element LSa plus the first lens group G1 is sufficient to make the lens module efficiently utilize the illumination light beam IL emitted by the first light emitting element LSa without a relay lens, i.e. without forming an intermediary image.

Figure 2A:
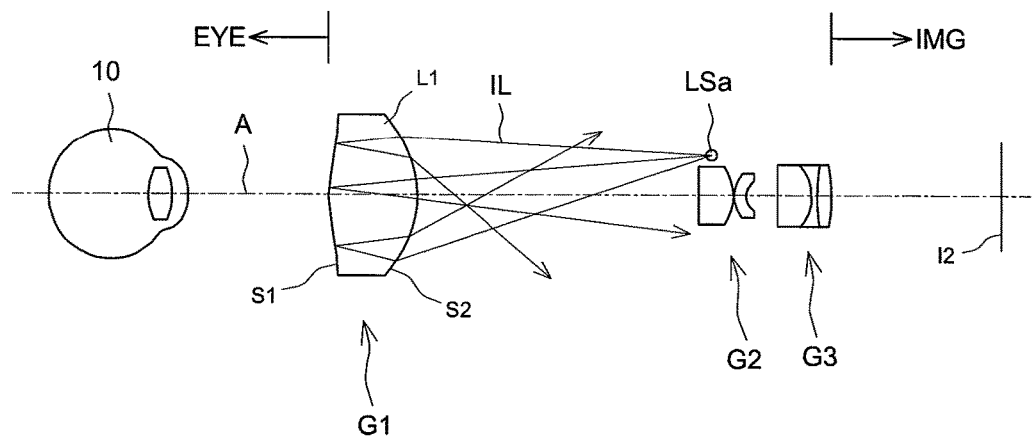
FIG. 2a and FIG. 2b schematically show that an illumination light beam is reflected by a first lens group of the lens module of the first embodiment of the present invention.
Figure 2B:
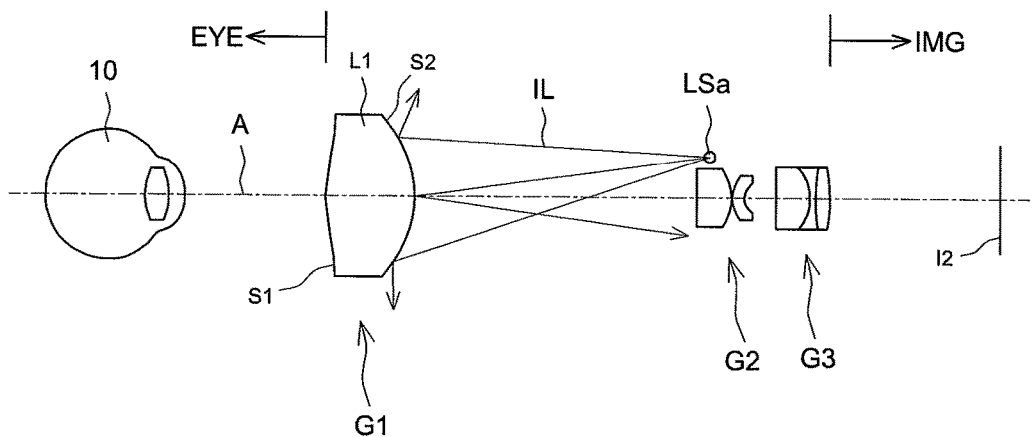

As light is unlikely to pass through a lens completely, a portion of the illumination light beam incident on the first lens group G1 is reflected to the imaging lens, i.e. the second lens group G2, forming the so-called ghost image. Refer to FIG. 2a and FIG. 2b. In one embodiment, the first lens group G1 of the lens module is a biconvex structure. The surface S1 of the first lens group G1 is a concave surface for the first light emitting element LSa. While the surface S1 reflects the illumination light beam IL, the illumination light beam IL is converged. The convex surface S2 refracts the reflected illumination light beam IL and further converges the reflected illumination light beam IL, whereby the light output angle of the reflected illumination light beam IL is increased furthermore, and whereby the reflected illumination light beam IL incident to the second lens group G2 is greatly decreased, as shown in FIG. 2a. The surface S2 of the first lens group G1 is a convex surface for the first light emitting element LSa. While the surface S2 reflects the illumination light beam IL, the illumination light beam IL is divergent. Thus, the reflected illumination light beam IL incident to the second lens group G2 is also greatly decreased, as shown in FIG. 2b. From the above description, it is learned: the biconvex design of the first lens group G1 greatly reduces the ghosting effect. Besides, adjusting the position of the first light emitting element LSa, i.e. adjusting the distance between the first light emitting element LSa and the optical axis A, can further reduce the ghosting effect.

Figure 3:
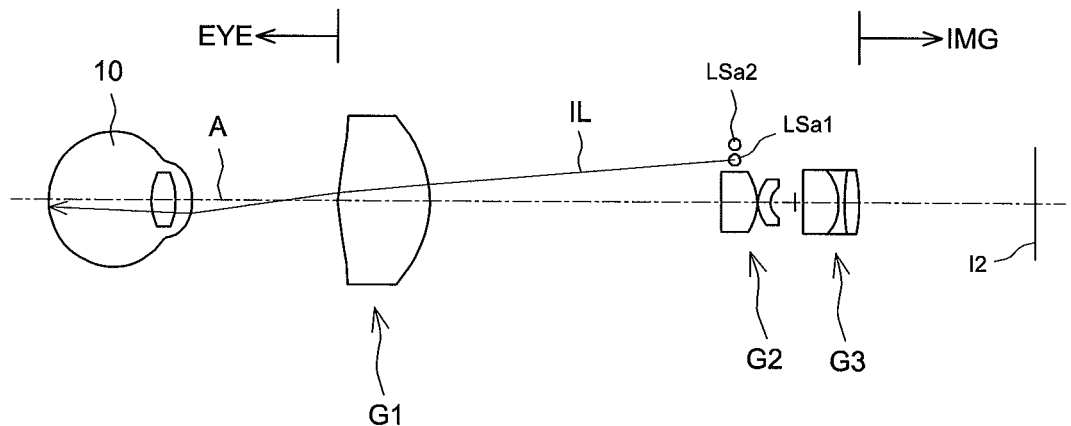
FIG. 3 schematically shows a lens module according to a second embodiment of the present invention.

In one embodiment, the first light emitting element LSa may be a visible light LED (Light Emitting Diode) or an infrared LED according to practical requirement. Refer to FIG. 3. In one embodiment, the first light emitting element LSa contains a plurality of LEDs, including visible light LEDs LSa1 and infrared LEDs LSa2. The proportions of visible light LEDs LSa1 and infrared LEDs LSa2 are designed according to practical requirement. For example, the first light emitting element LSa contains two pieces of visible light LEDs LSa1 and one piece of infrared LED LSa2. In order to make the positions of the first light emitting element LSa and the cornea of the eyeball 10 meet the object-image relationship, the visible light LED LSa1 and the infrared LED LSa2 may be arranged one above one, i.e. the visible light LED LSa1 and the infrared LED LSa2 are respectively separated from the optical axis A by different distances, as shown in FIG. 3. Alternatively, the visible light LED LSa1 and the infrared LED LSa2 are arranged side by side, i.e. the visible light LED LSa1 and the infrared LED LSa2 are equidistant to the optical axis A. It should be noted that the positions of the visible light LED LSa1 and the infrared LED LSa2 may be interchanged top and bottom or left and right; the visible light LED LSa1 and the infrared LED LSa2 may also be arranged in annular symmetry.

Figure 4:
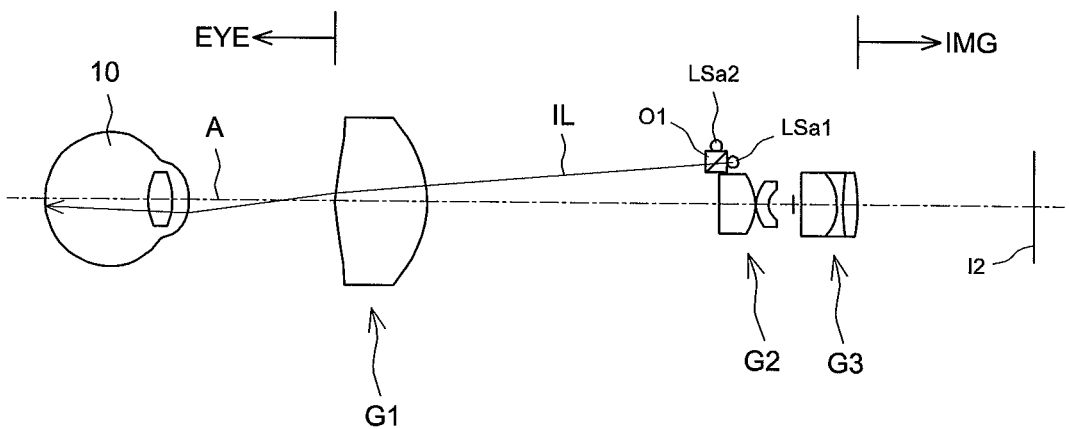
FIG. 4 schematically shows a lens module according to a third embodiment of the present invention.

Refer to FIG. 4. In one embodiment, the lens module of the present invention further comprises an optical element O1 arranged between the first lens group G1 and the first light emitting element LSa. The optical element O1 diverts the illumination light beam IL to the first lens group G1. For example, the optical element O1 is realized by a polarizer, a prism or a beam splitter. As shown in FIG. 4, the illumination light beam IL emitted by the infrared LED LSa2 is diverted by the optical element O1, whereby the virtual position from which the infrared light beam seems to be emitted is identical to the position where the visible light LED LSa1 is located, and whereby the virtual position of the infrared LED LSa2 and the position of the visible light LED LSa1 are equidistant to the optical axis A and on the same object plane. Therefore, the illumination field of the infrared LED LSa2 is very close to that of the visible light LED LSa1.

Figure 5:
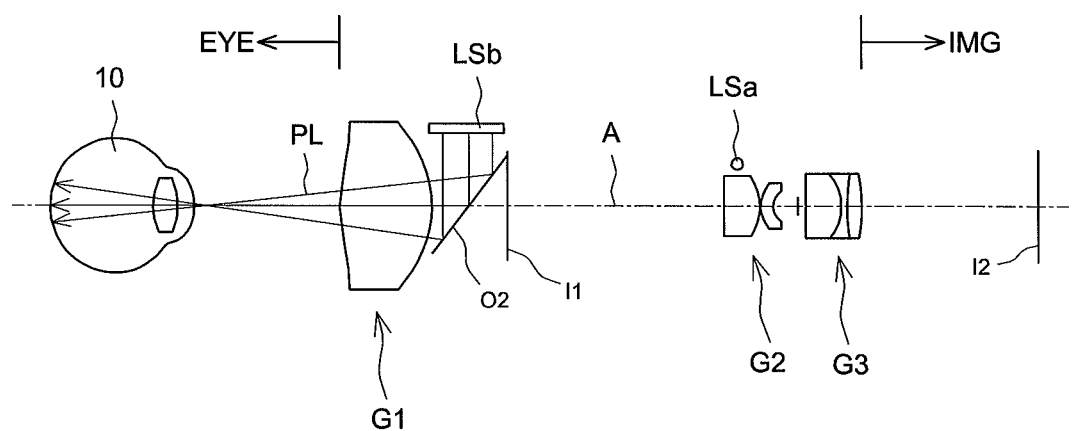
FIG. 5 schematically shows a lens module according to a fourth embodiment of the present invention.

Refer to FIG. 5. In one embodiment, the lens module of the present invention further comprises a second light emitting element LSb generating a precision light beam PL. The precision light beam PL is reflected by a beam splitter O2, and the first lens group G1 converges the reflected precision light beam PL to the cornea in the eye fundus side EYE. The precision light beam PL reflected by the beam splitter O2 seems to be emitted from the position of the intermediary image I1 of the lens module. Therefore, the second light emitting element LSb is equivalently located at the position of the intermediary image I1. According to the foregoing structure, the precision light beam PL emitted by the second light emitting element LSb is incident to the fundus of the eyeball 10; the tester ignites the second light emitting element LSb disposed at a special position, and the testee gazes at the ignited second light emitting element LSb, whereby the eyeball 10 of the testee is fixed to a special angle.

Figure 6A:
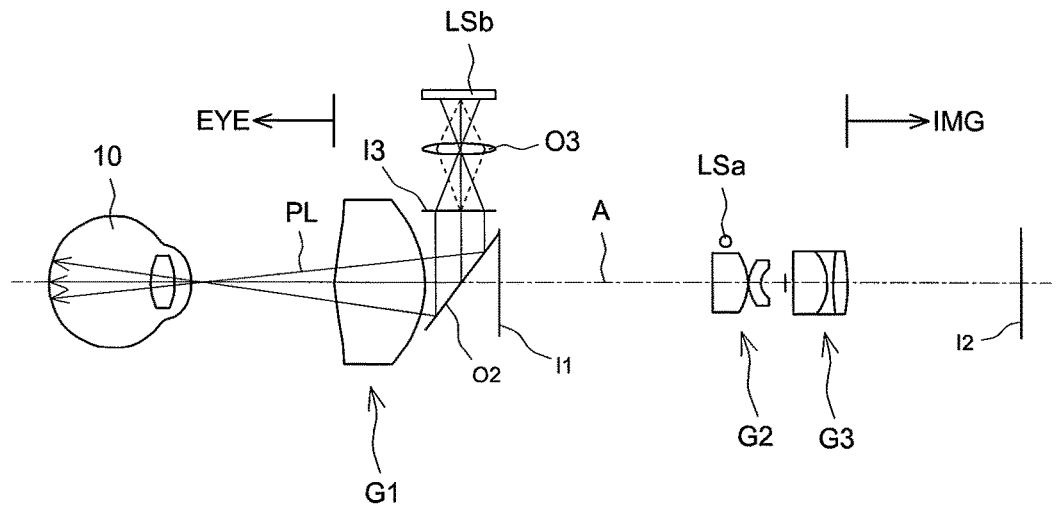
FIG. 6a schematically shows a lens module according to a fifth embodiment of the present invention.
Figure 6B:
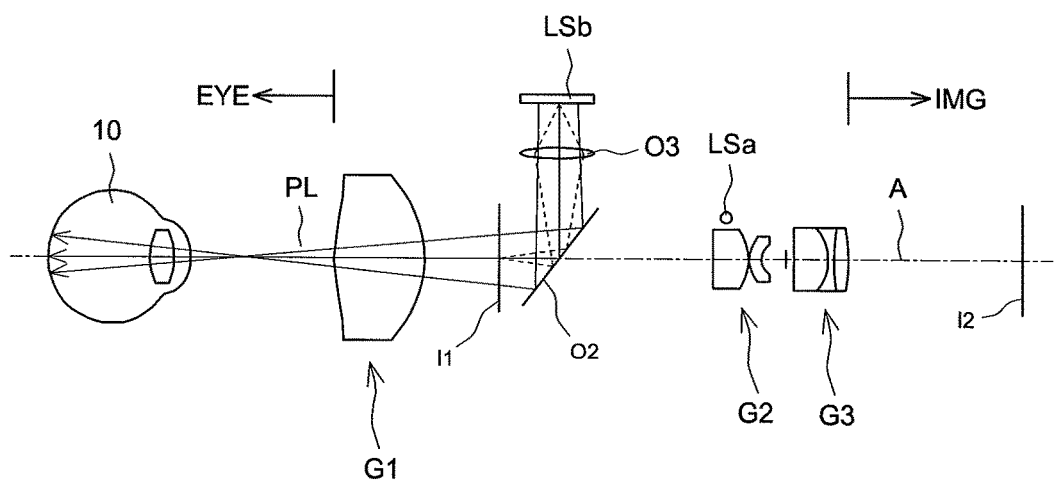
FIG. 6b schematically shows a lens module according to a sixth embodiment of the present invention.

Refer to FIG. 6a and FIG. 6b. In one embodiment, the lens module further comprises an optical lens O3 arranged between the second light emitting element LSb and the beam splitter O2. The optical lens O3 converges the precision light beam PL generated by the second light emitting element LSb to form an intermediary image, whereby the second light emitting element LSb is equivalently located at the position of the intermediary image I1 of the lens module. For example, as shown in FIG. 6a, the optical lens O3 converges the precision light beam PL to form an intermediary image I3 before the beam splitter O2. The precision light beam PL reflected by the beam splitter O2 is equivalently emitted by a virtual second light emitting element LSb located at the position of the intermediary image I1. Alternatively, as shown in FIG. 6b, the precision light beam PL generated by the second light emitting element LSb is converged by the optical lens O3 and reflected by the beam splitter O2 to form an intermediary image located at the position of the intermediary image I1. Via appropriate design, the beam splitter O2 for reflecting the precision light beams PL may be arranged in the eye fundus side EYE or the image side IMG of the intermediary image I1 of the lens module.

Below, embodiments are used to further demonstrate the lens module of the present invention. Refer to Table.1, which defines the parameters of the lens module shown in FIG. 1. The surface numbers are corresponding to the surfaces of the lenses in FIG. 1. The surface S7 is a surface of a diaphragm. The thickness is the distance between the current surface and the next surface in the image side IMG along the optical axis A. For example, the value in the field of thickness corresponding to the surface S1 is the distance between the surface S1 and the surface S2 along the optical axis A; the value in the field of thickness corresponding to the surface S11 is the distance between the surface S11 and the image I2 along the optical axis A. An asterisk labeled on a surface number means that the surface is an aspherical surface.

TABLE 1

| Surface Number | Radius of Curvature (mm) | Thickness (mm) | Refractivity | Dispersion Coefficient |
| --- | --- | --- | --- | --- |
| S1* | 29.00 | 15.30 | 1.545 | 55.930 |
| S2* | −16.00 | 49.00 | | |
| S3* | −136.50 | 6.00 | 1.545 | 55.930 |
| S4* | −5.26 | 0.20 | | |
| S5* | 4.23 | 2.00 | 1.585 | 29.909 |
| S6* | 1.93 | 5.00 | | |
| S7 (diaphragm) | ∞ | 0.50 | | |
| S8 | −1000.00 | 6.00 | 1.806 | 40.926 |
| S9 | −6.60 | 0.80 | 1.785 | 26.291 |
| S10 | 27.45 | 2.56 | 1.678 | 55.341 |
| S11 | −17.66 | 28.87 | | |

An aspherical surface can be expressed by an equation:

$$z = \frac{cr^2}{1 + \sqrt{1 - (1+k)c^2 r^2}} + \alpha_1 r^2 + \alpha_2 r^4 + \alpha_3 r^6 + \alpha_4 r^8 + \alpha_5 r^{10} + \alpha_6 r^{12} + \alpha_7 r^{14} + \alpha_8 r^{16}$$

wherein c is the paraxial curvature, r is the distance between the surface of a lens and the optical axis A, z is the distance between Point on the aspherical surface with the distance r and the tangential plane of the vertex of the aspherical surface (a plane vertical to the optical axis A), k is the ellipsoidal coefficient, $\alpha_{1-8}$ are the coefficients. The coefficients of the aspherical surface are listed in Table.2. The coefficients $\alpha_1$, $\alpha_7$ and $\alpha_8$ are not listed in Table.2, and the values thereof are zero.

TABLE 2

| Surface Number | k | $\alpha_2$ | $\alpha_3$ | $\alpha_4$ | $\alpha_5$ | $\alpha_6$ |
| --- | --- | --- | --- | --- | --- | --- |
| S1 | — | −4.35546E−05 | 1.17552E−07 | −3.28706E−09 | 2.41621E−11 | −5.88136E−14 |
| S2 | −0.056640 | 2.58458E−05 | 3.72384E−08 | −3.72701E−10 | 2.08903E−12 | 1.52052E−15 |
| S3 | — | −1.16402E−04 | −1.54925E−05 | −6.10529E−07 | 6.41977E−08 | −1.08872E−09 |
| S4 | −4.504411 | — | −5.79017E−05 | 4.11551E−06 | −1.26210E−07 | 1.85650E−09 |
| S5 | — | −4.13656E−03 | 1.26750E−05 | 1.84683E−07 | 9.22369E−08 | — |
| S6 | −1.770931 | — | 1.39303E−04 | −2.19843E−05 | 6.05103E−06 | — |

Refer to FIG. 1 again. In one embodiment, the eye fundus camera of the present invention comprises an image sensing module 20 and a lens module. The lens module comprises a first lens group G1, a second lens group G2 and a third lens group G3. The detailed structure of the lens module has been described hereinbefore and will not repeat herein. The image sensing module 20 senses light and forms an image. In FIG. 1, a gap is depicted between the image I2 and the image sensing module 20 to signify that they are different objects. In fact, the image I2 should be formed on the sensing surface of the image sensing module 20.

In one embodiment, the eye fundus camera of the present invention further comprises a display module 30 electrically connected with the image sensing module 20 and presenting the image I2. Thereby, the observer can observe the image of the eye fundus of the testee without approaching the testee closely. In one embodiment, the eye fundus camera of the present invention further comprises a storage module 40 electrically connected with the image sensing module 20 and storing the images I2 captured by the image sensing module 20 as records. Via comparing the records, the physician can determine the extent of recovery.

In conclusion, the lens module and the eye fundus camera share one of the lens groups with the illumination system, whereby the illumination system is exempted from using any additional lens, and whereby the volume of the system is reduced. Thus, the present invention is easy to carry about and applicable to far-end healthcare. The shared lens group is a biconvex-surface design, which can decrease the incidence of the light reflected by the shared lens group to the imaging system and reduce the ghosting effect. Further, the precision light beam also shares the same lens group and need not use any additional lens. The handheld eye fundus camera can provide a precision light beam to help the testee turn his eyeball to a specified angle, whereby the observer can easily observe the fundus of the eye.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. A lens module, used to converge an image light beam reflected from an eye fundus, and comprising a first lens group, a second lens group and a third lens group, which are arranged from an eye fundus object side to an image side in sequence, and a first light emitting element, wherein:
    said first lens group has a positive effective focal length and is a single whole lens having two convex surfaces respectively facing said eye fundus object side and said image side;
    said second lens group has a negative effective focal length and includes a plurality of second lenses, and wherein a lens of said second lenses closest to said eye fundus object side has a concave surface facing said eye fundus object side; and
    said third lens group has a positive effective focal length and includes a plurality of third lenses, wherein at least one said third lens is a cemented lens; and
    said first light emitting element is arranged in said image side of said first lens group and at a single position separated from a surface of said first lens, which faces said image side by a distance of 40-100 mm, and deviated from an optical axis of said lens module, and which is used to generate an illumination light beam and directly irradiate said first lens group to define an illumination range on said first lens group, wherein said illumination light beam is converged solely by said first lens group to a cornea on said object side and said illumination range contains a central area of said first lens group.

2. The lens module according to claim 1, wherein positions of said first light emitting element and said cornea meets an object-image relationship of said first lens group.

3. The lens module according to claim 1, wherein said first light emitting element includes a plurality of light emitting diodes (LEDs), and wherein said plurality of LEDs includes at least one of visible light LEDs and infrared LEDs.

4. The lens module according to claim 1 further comprising a second light emitting element generating a precision light beam, wherein said precision light beam is reflected to said first lens group by a beam splitter, and said first lens group converges said precision light beam to a cornea in said eye fundus side, and wherein said precision light beam is equivalently emitted from a position of a first intermediary image of said lens module.

5. The lens module according to claim 4 further comprising an optical lens arranged between said second light emitting element and said beam splitter, wherein said optical lens converges said precision light beam, which is emitted by said second light emitting element, to form a second intermediary image, and wherein positions of said second intermediary image and said first intermediary image of said lens module is equivalent.

6. An eye fundus camera comprising
    an image sensing module sensing light to form an image; and
    a lens module, used to converge an image light beam reflected from an eye fundus to said image sensing module and comprising a first lens group, a second lens group and a third lens group, which are arranged from an object side to an image side in sequence, and a first light emitting element, wherein:
    said first lens group has a positive effective focal length and is a single whole lens having two convex surfaces respectively facing said object side and said image side;
    said second lens group has a negative effective focal length and includes a plurality of second lenses, and wherein a lens of said second lenses closest to said object side has a concave surface facing said object side; and
    said third lens group has a positive effective focal length and includes a plurality of third lenses, wherein at least one said third lens is a cemented lens; and
    said first light emitting element is arranged in said image side of said first lens group and at a single position separated from a surface of said first lens, which faces said image side, by a distance of 40-100 mm, and deviated from an optical axis of said lens module, and which is used to generate an illumination light beam and directly irradiate said first lens group to define an illumination range on said first lens group, wherein said illumination light beam is converged solely by said first lens group to a cornea on said object side and said illumination range contains a central area of said first lens group.

7. The eye fundus camera according to claim 6, wherein positions of said first light emitting element and said cornea meets an object-image relationship of said first lens group.

8. The eye fundus camera according to claim 6, wherein said first light emitting element includes a plurality of light emitting diodes (LEDs), and wherein said plurality of LEDs includes at least one of visible light LEDs and infrared LEDs.

9. The eye fundus camera according to claim 6 further comprises a second light emitting element generating a precision light beam, wherein said precision light beam is reflected to said first lens group by a beam splitter, and said first lens group converges said precision light beam to a cornea in said eye fundus side, and wherein said precision light beam is equivalently emitted from a position of a first intermediary image of said lens module.

10. The eye fundus camera according to claim 9 further an optical lens arranged between said second light emitting element and said beam splitter, wherein said optical lens converges said precision light beam, which is emitted by said second light emitting element, to form a second intermediary image, and wherein positions of said second intermediary image and said first intermediary image of said lens module is equivalent.

11. The eye fundus camera according to claim 6 further comprises a display module electrically connected with said image sensing module to present said image.

12. The eye fundus camera according to claim 6 further comprises a storage module electrically connected with said image sensing module to store said image.

* * * * *